United States Patent
Meek et al.

(10) Patent No.: US 9,615,941 B2
(45) Date of Patent: *Apr. 11, 2017

(54) ORTHOPEDIC TOOL FOR ALTERING THE CONNECTION BETWEEN ORTHOPEDIC COMPONENTS

(71) Applicant: Zimmer, Inc., Warsaw, IN (US)

(72) Inventors: Christopher M. S. Meek, Leesburg, IN (US); Shaun R. Cronin, Warsaw, IN (US); Peter Darrigan, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/704,358

(22) Filed: May 5, 2015

(65) Prior Publication Data
US 2015/0230940 A1    Aug. 20, 2015

Related U.S. Application Data

(63) Continuation of application No. 13/875,467, filed on May 2, 2013, now abandoned, which is a continuation
(Continued)

(51) Int. Cl.
*A61F 2/46* (2006.01)
*A61B 17/88* (2006.01)
*A61F 2/38* (2006.01)

(52) U.S. Cl.
CPC ............ *A61F 2/4637* (2013.01); *A61B 17/88* (2013.01); *A61F 2/38* (2013.01); *A61F 2002/4641* (2013.01)

(58) Field of Classification Search
CPC .................. A61F 2/4603; A61F 2/4637; A61F 2002/4619; A61F 2002/4624; A61F 2002/4627; A61F 2002/4641
(Continued)

(56) References Cited

U.S. PATENT DOCUMENTS 1,959,008 A    5/1934   Spaloss
2,747,448 A *  5/1956   McCafferty ............. B25B 13/54
                                                         81/445
(Continued)

FOREIGN PATENT DOCUMENTS

DE    3023942 A1    1/1982
DE    4441870 C1    3/1996
(Continued)

OTHER PUBLICATIONS

"U.S. Appl. No. 11/743,385, Final Office Action mailed Jan. 25, 2010", 6 pgs.
(Continued)

*Primary Examiner* — Matthew Lawson
*Assistant Examiner* — Amy Sipp
(74) *Attorney, Agent, or Firm* — Schwegman Lundberg & Woessner, P.A.

(57) ABSTRACT

An orthopedic tool for loosening the connection between orthopedic components. In one embodiment, the orthopedic tool includes a housing and a wedge. The housing has a head, an upper portion, a lower portion, and an opening between the upper and lower portions. The wedge is positioned at least partially between the upper portion and the lower portion of the housing and is actuatable to move toward the head of the housing. When at least a portion of the head of the housing is placed in mating engagement with the junction between two assembled orthopedic components, advancement of the wedge towards the head results in separation of the upper portion and lower portion of the housing. Thus, as the wedge is advanced toward the head, the upper and lower portions of the housing are separated, which results in corresponding separation of the assembled orthopedic components.

17 Claims, 13 Drawing Sheets

Related U.S. Application Data of application No. 11/743,485, filed on May 2, 2007, now Pat. No. 8,435,244.

(58) Field of Classification Search
USPC .................................................. 606/99, 100
See application file for complete search history.

(56) References Cited

U.S. PATENT DOCUMENTS

| | | | |
|---|---|---|---|
| 3,549,159 A | | 12/1970 | Kroener |
| 3,574,381 A | * | 4/1971 | Ocheltree ............... B25B 9/00 |
| | | | 294/94 |
| 3,801,989 A | | 4/1974 | McKee |
| 4,459,985 A | | 7/1984 | Mckay et al. |
| 4,642,121 A | * | 2/1987 | Keller ................ A61F 2/3609 |
| | | | 606/99 |
| 4,686,971 A | * | 8/1987 | Harris ................ A61F 2/4607 |
| | | | 606/99 |
| 4,865,609 A | | 9/1989 | Roche |
| 5,061,270 A | * | 10/1991 | Aboczky ............... A61F 2/4609 |
| | | | 606/91 |
| 5,122,130 A | * | 6/1992 | Keller ................ A61B 17/025 |
| | | | 606/205 |
| 5,352,227 A | | 10/1994 | O'hara |
| 5,431,658 A | | 7/1995 | Moskovich |
| 5,489,311 A | | 2/1996 | Cipolletti |
| 5,571,111 A | * | 11/1996 | Aboczky ............... A61F 2/4609 |
| | | | 606/91 |
| 5,683,395 A | * | 11/1997 | Mikhail ............... A61F 2/4601 |
| | | | 606/86 R |
| 6,063,124 A | * | 5/2000 | Amstutz ................ A61F 2/34 |
| | | | 623/22.21 |
| 6,136,004 A | * | 10/2000 | Keller ................ A61B 17/921 |
| | | | 606/104 |
| 6,224,599 B1 | * | 5/2001 | Baynham ............ A61B 17/025 |
| | | | 606/79 |
| 6,258,090 B1 | | 7/2001 | Jackson |
| 6,286,401 B1 | | 9/2001 | Hajianpour |
| 6,565,570 B2 | | 5/2003 | Sterett et al. |
| 6,770,074 B2 | * | 8/2004 | Michelson .......... A61B 17/025 |
| | | | 606/80 |
| 7,621,921 B2 | | 11/2009 | Parker |
| 8,142,439 B2 | | 3/2012 | Parker |
| 8,152,814 B2 | | 4/2012 | Jones et al. |
| 8,303,601 B2 | | 11/2012 | Bandeira et al. |
| 8,435,244 B2 | | 5/2013 | Meek et al. |
| 2002/0004684 A1 | | 1/2002 | Thomas et al. |
| 2003/0036764 A1 | * | 2/2003 | Hamada ............. A61B 17/1604 |
| | | | 606/102 |
| 2004/0225295 A1 | * | 11/2004 | Zubok ..................... A61F 2/442 |
| | | | 606/90 |
| 2005/0038444 A1 | * | 2/2005 | Binder, Jr. .......... A61B 17/1728 |
| | | | 606/96 |
| 2005/0143747 A1 | | 6/2005 | Zubok et al. |
| 2006/0241641 A1 | | 10/2006 | Albans et al. |
| 2007/0078464 A1 | * | 4/2007 | Jones .................... A61F 2/4637 |
| | | | 606/86 R |
| 2007/0123904 A1 | | 5/2007 | Stad et al. |
| 2013/0289634 A1 | | 10/2013 | Meek et al. |

FOREIGN PATENT DOCUMENTS

| | | |
|---|---|---|
| EP | 0121491 A1 | 10/1984 |
| EP | 0145641 A1 | 6/1985 |
| EP | 1106148 A1 | 6/2001 |

OTHER PUBLICATIONS

"U.S. Appl. No. 11/743,385, Non Final Office Action mailed Jun. 23, 2009", 5 pgs.

"U.S. Appl. No. 11/743,385, Response filed Apr. 16, 2010 to Final Office Action mailed Jan. 25, 2010", 11 pgs.

"U.S. Appl. No. 11/743,385, Response filed May 29, 2009 to Restriction Requirement mailed Apr. 29, 2009", 2 pgs.

"U.S. Appl. No. 11/743,385, Response filed Sep. 22, 2009 to Non Final Office Action mailed Jun. 23, 2009", 11 pgs.

"U.S. Appl. No. 11/743,385, Restriction Requirement mailed Apr. 29, 2009", 5 pgs.

"U.S. Appl. No. 11/743,485, Notice of Allowance mailed Jan. 7, 2013", 11 pgs.

"U.S. Appl. No. 13/875,467, Final Office Action mailed Feb. 12, 2015", 14 pgs.

"U.S. Appl. No. 13/875,467, Non Final Office Action mailed Oct. 22, 2014", 13 pgs.

"U.S. Appl. No. 13/875,467, Response filed Jan. 12, 2015 to Non Final Office Action mailed Oct. 22, 2014", 13 pgs.

"Surgical Protocol", GMRS Distal Femoral Global Modular Replacement System, Stryker Orthopaedics, (2004), 1-49.

"Surgical Technique", Guardian Limb Salvage System, Total Femoral Replacement, Wright Medical Technology, (2001), 1-16.

"Surgical Technique", Orthogenesis LPS (Limb Preservation system) Lower Extremities. DePuy, (2003), 1-28.

Malawar, Martin M., "Surgical Technique", MRS Modular Replacement system, Distal Femoral Resection for Large Segmental Replacements, Howmedica, (1998), 1-44.

* cited by examiner

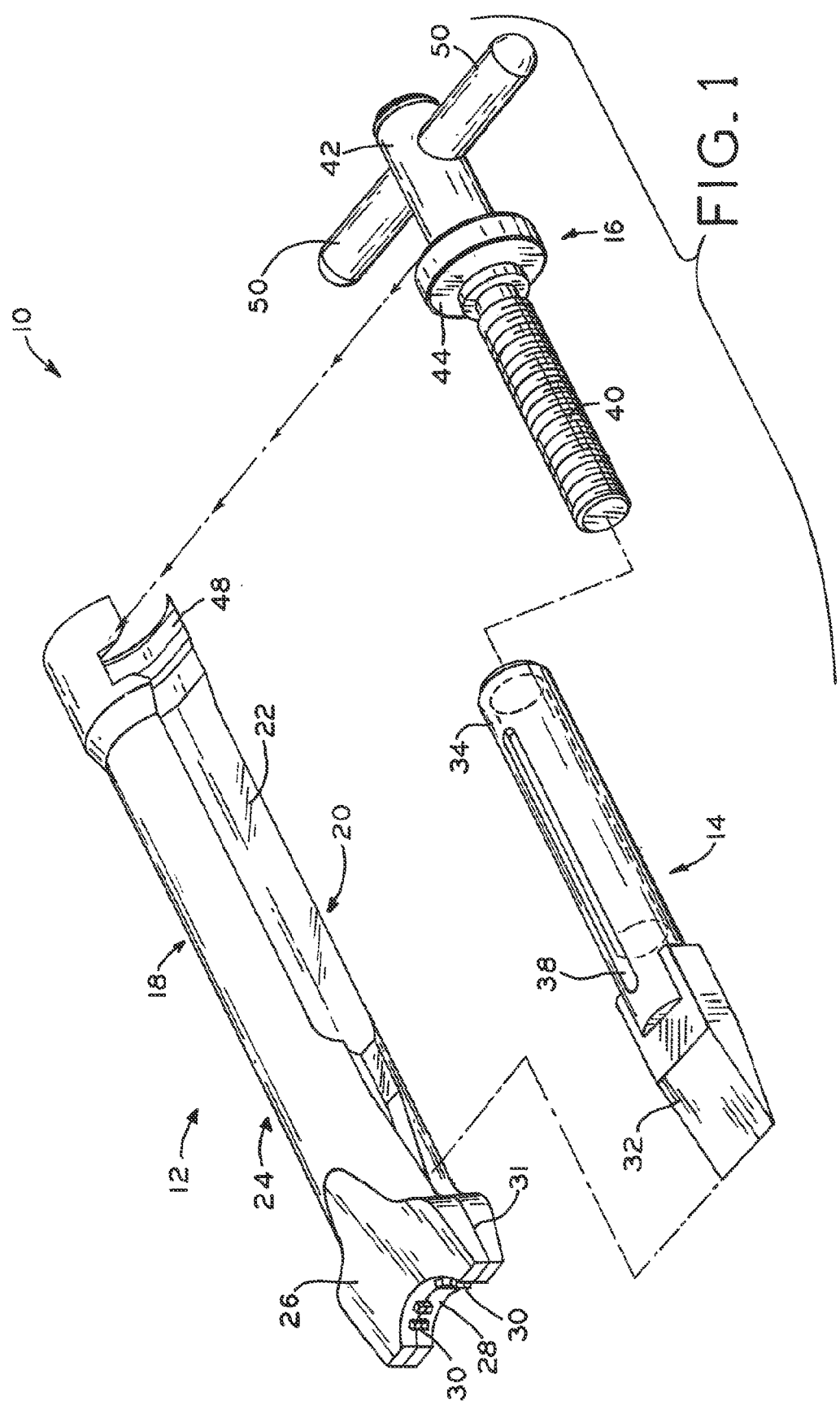

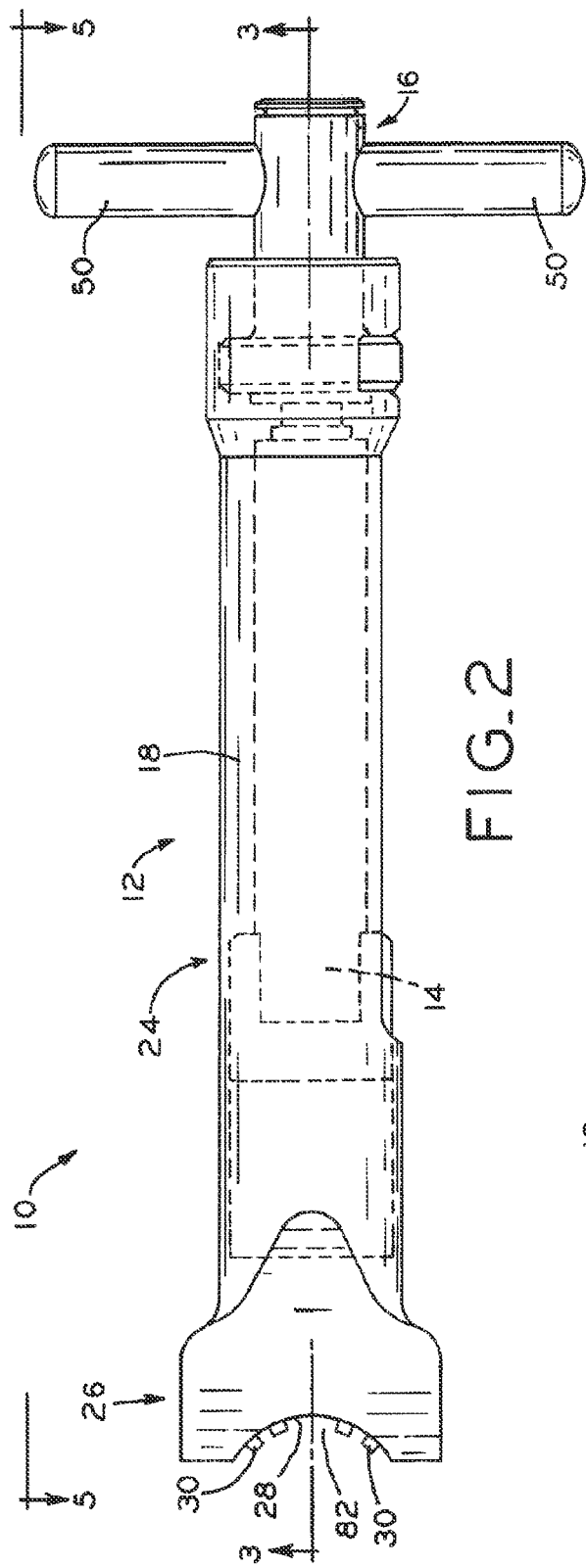
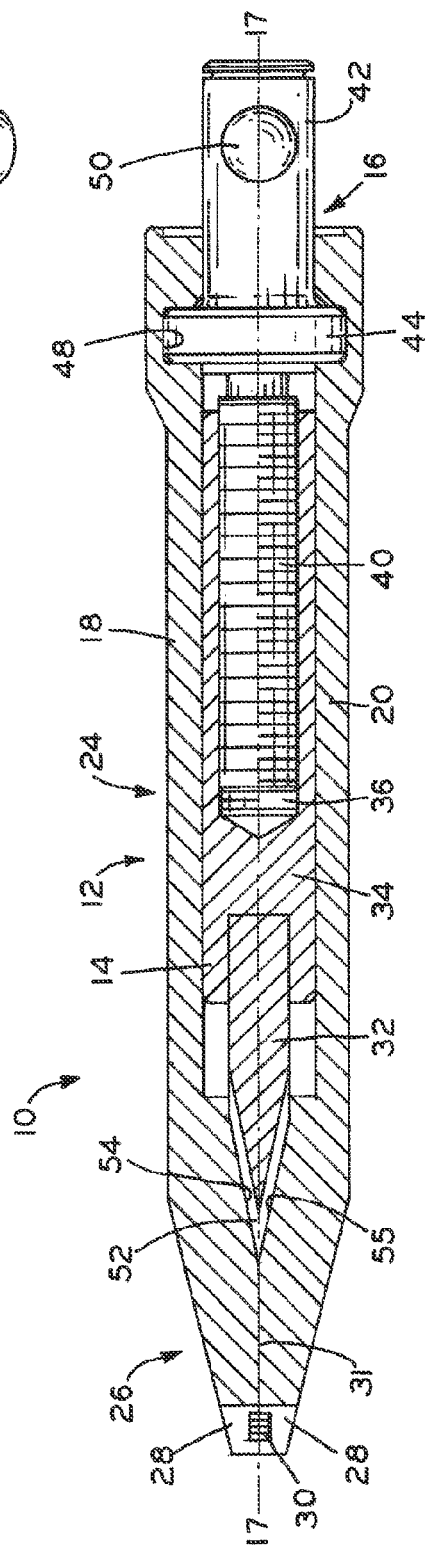

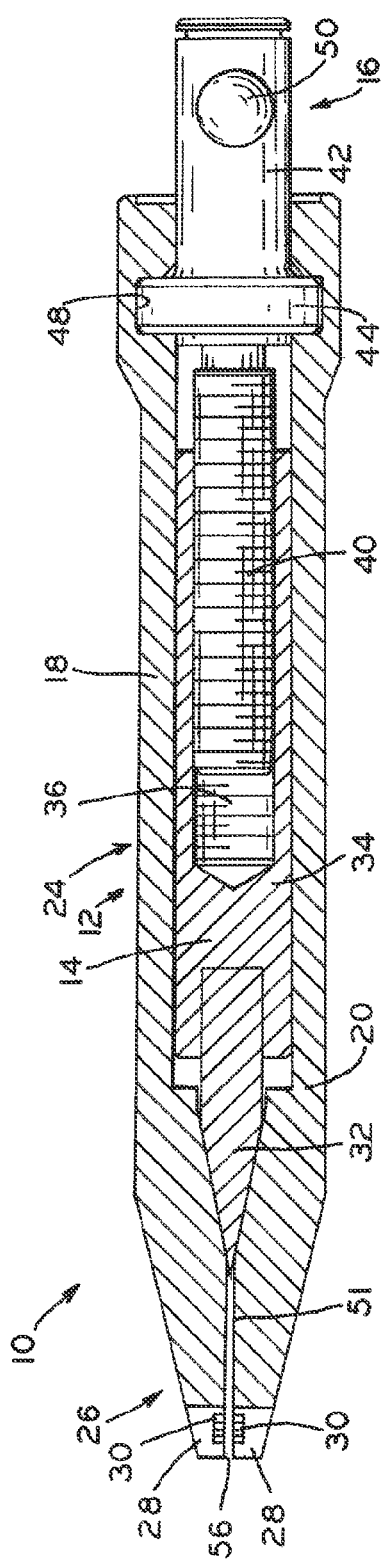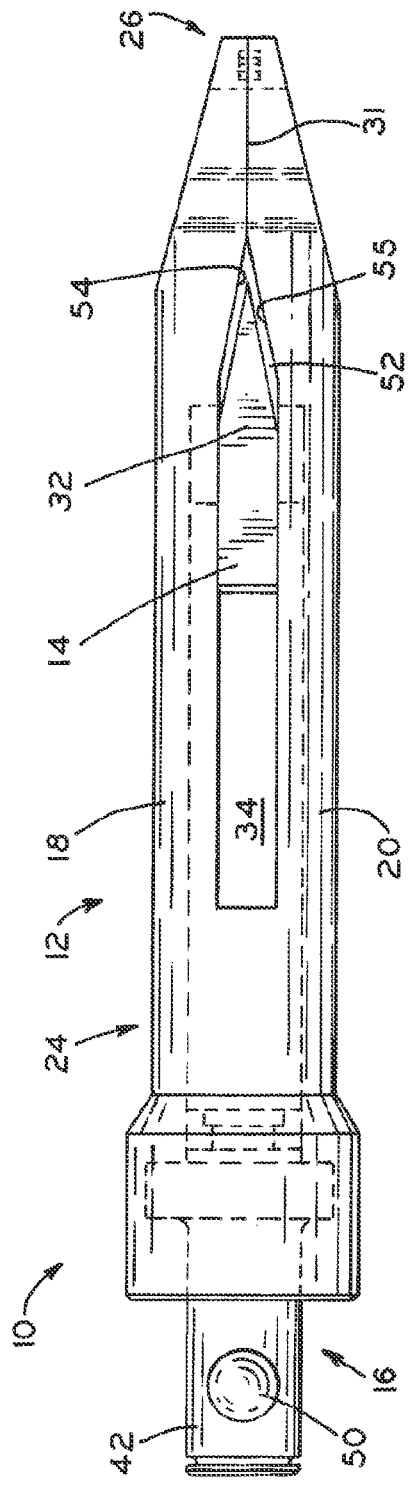

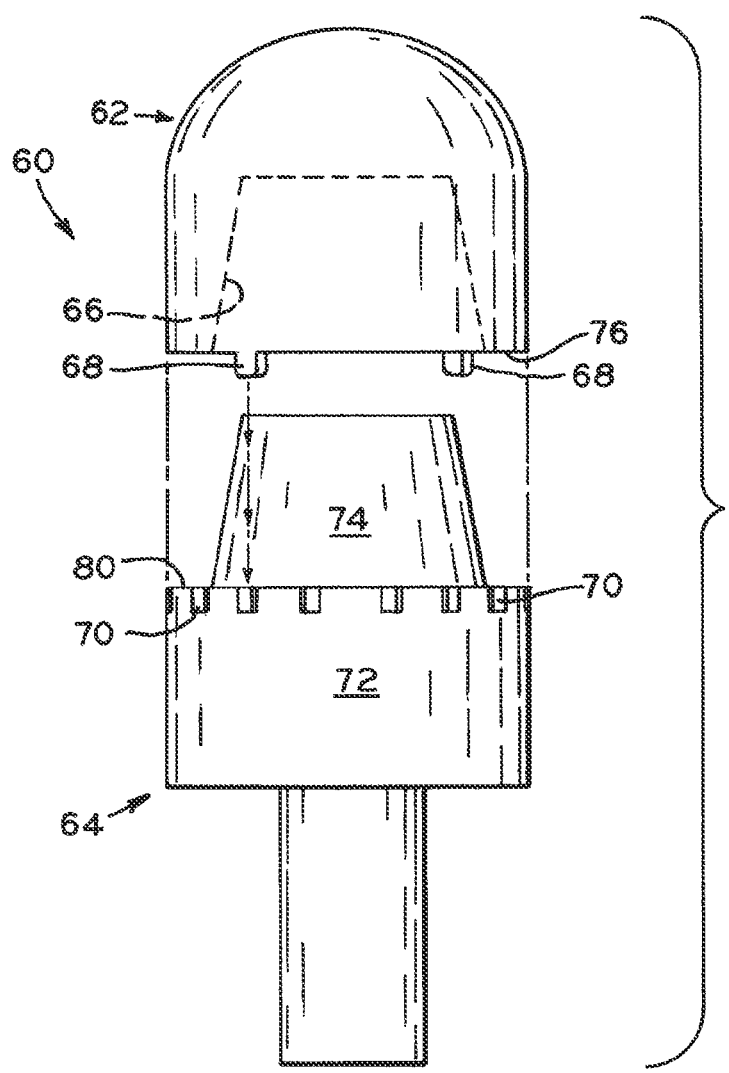

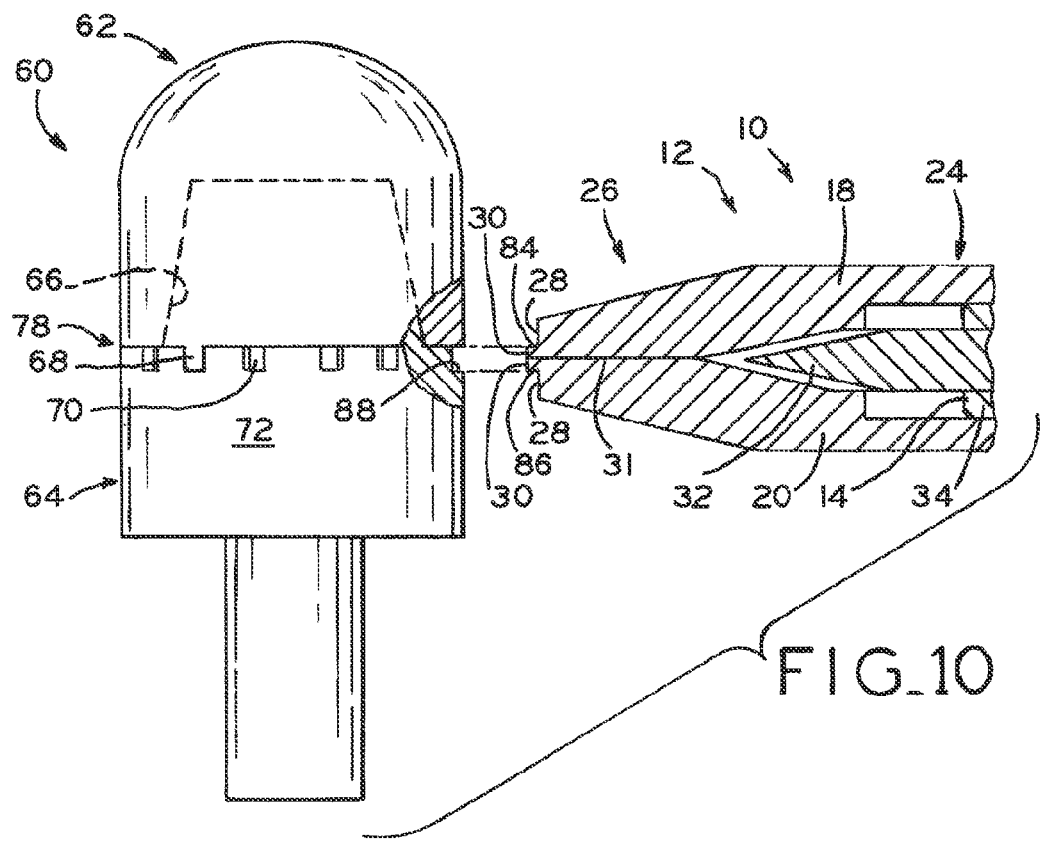
FIG_10
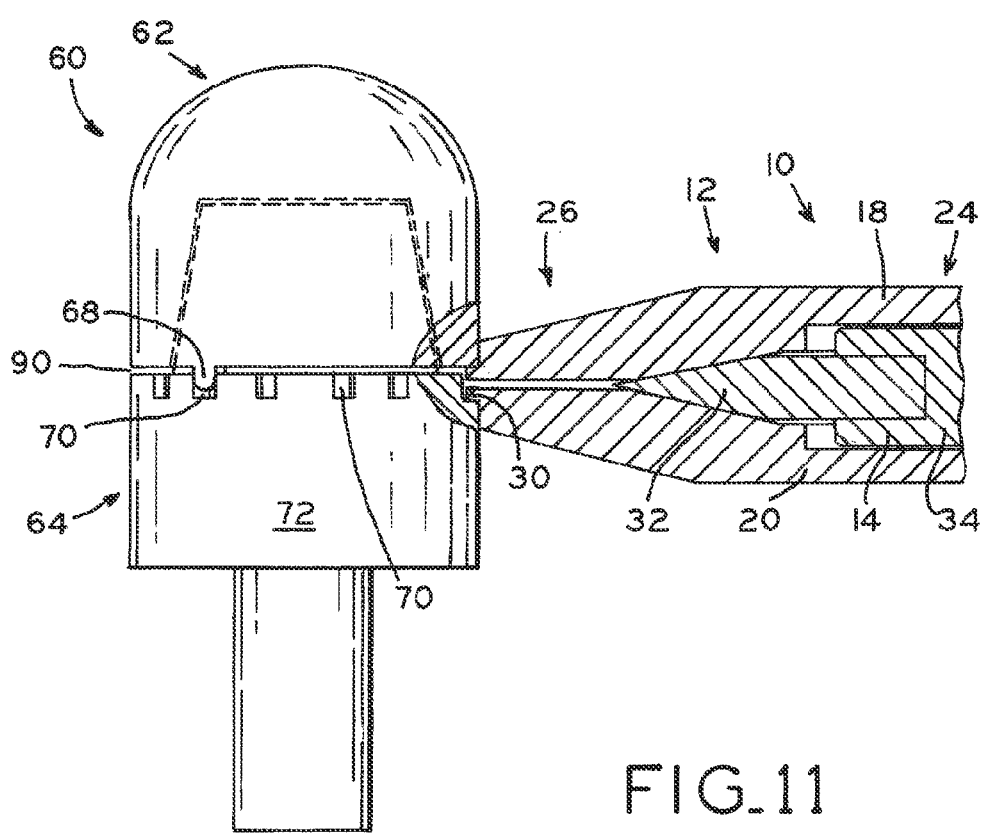
FIG_11

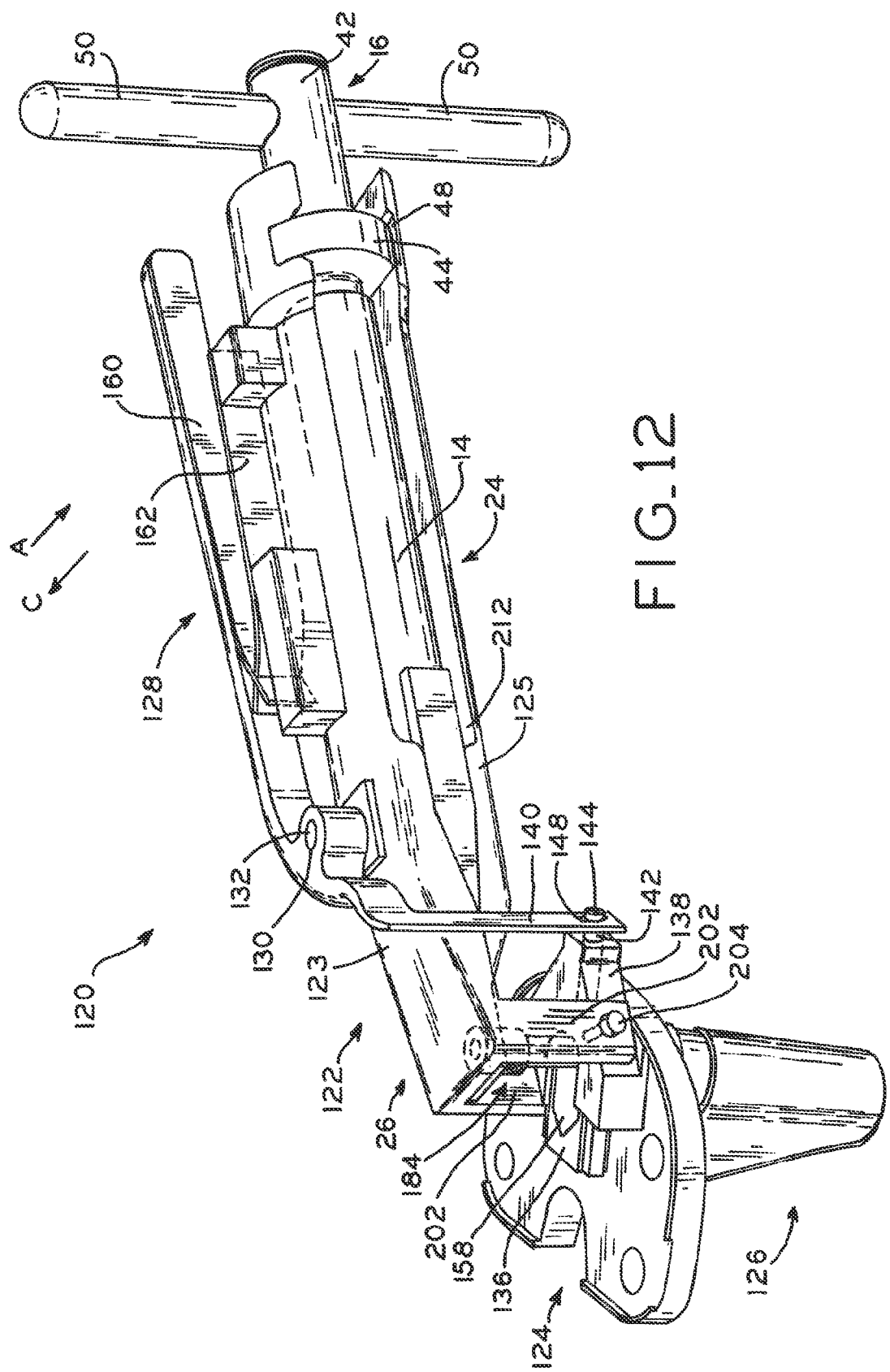

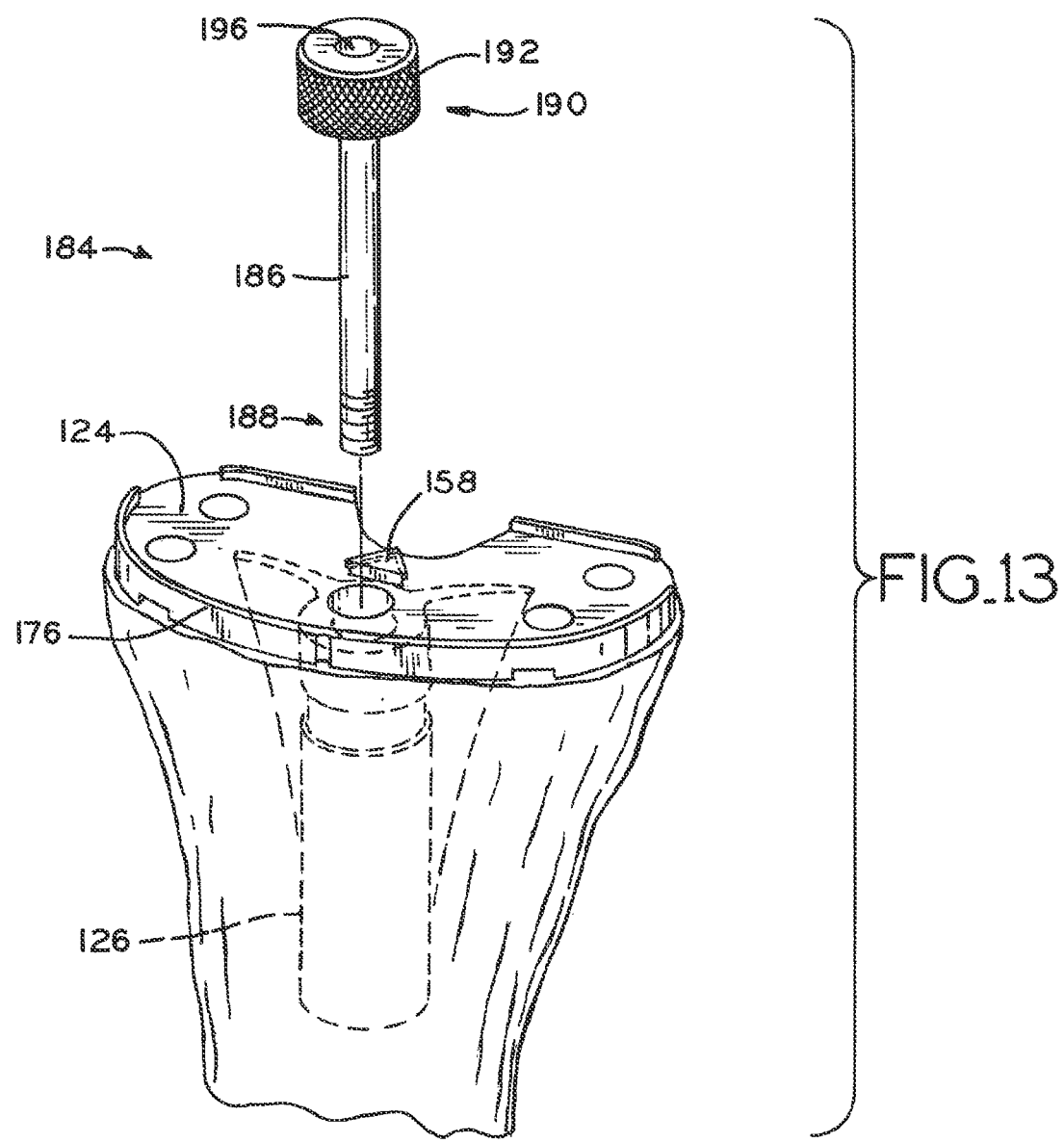

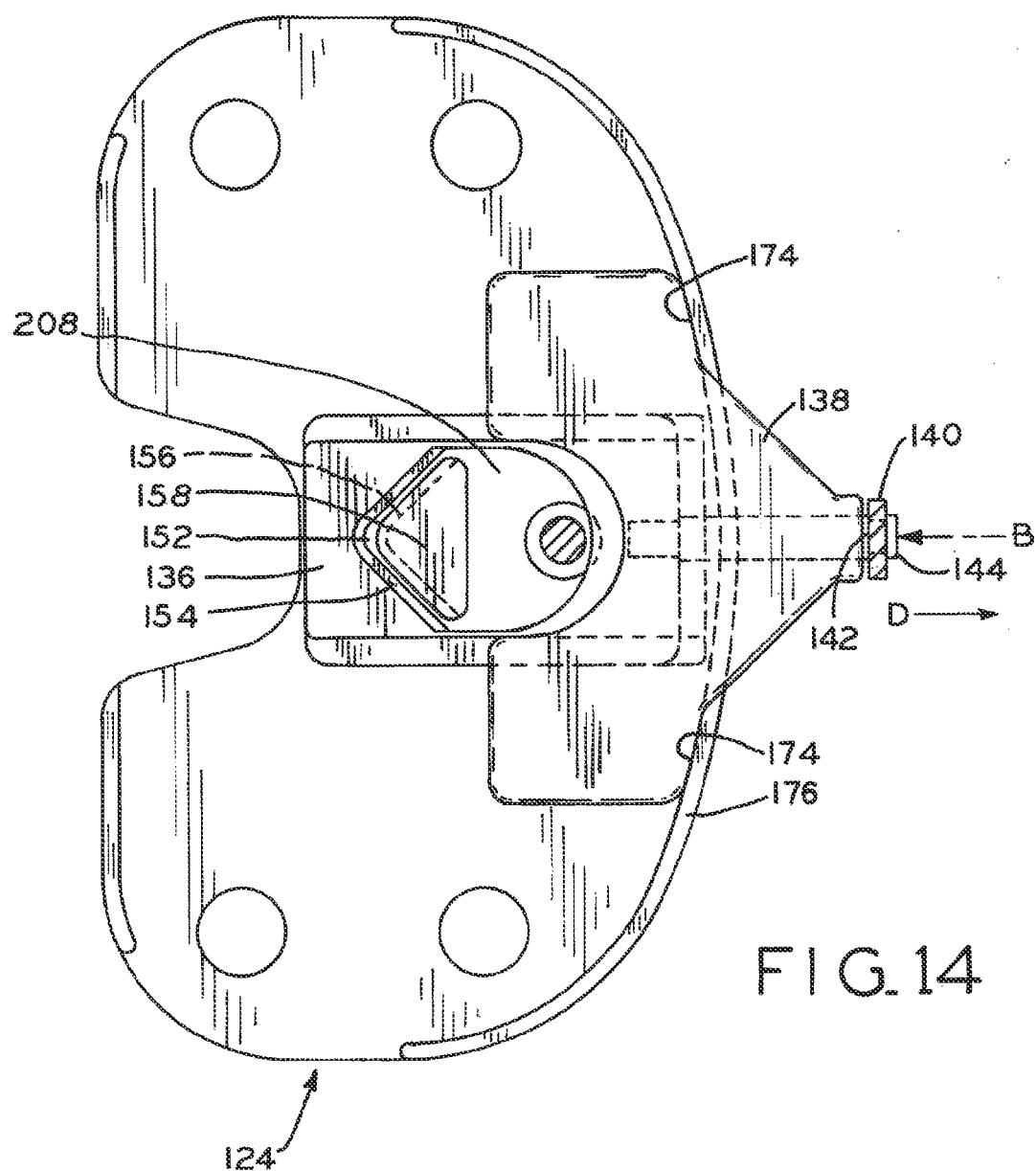

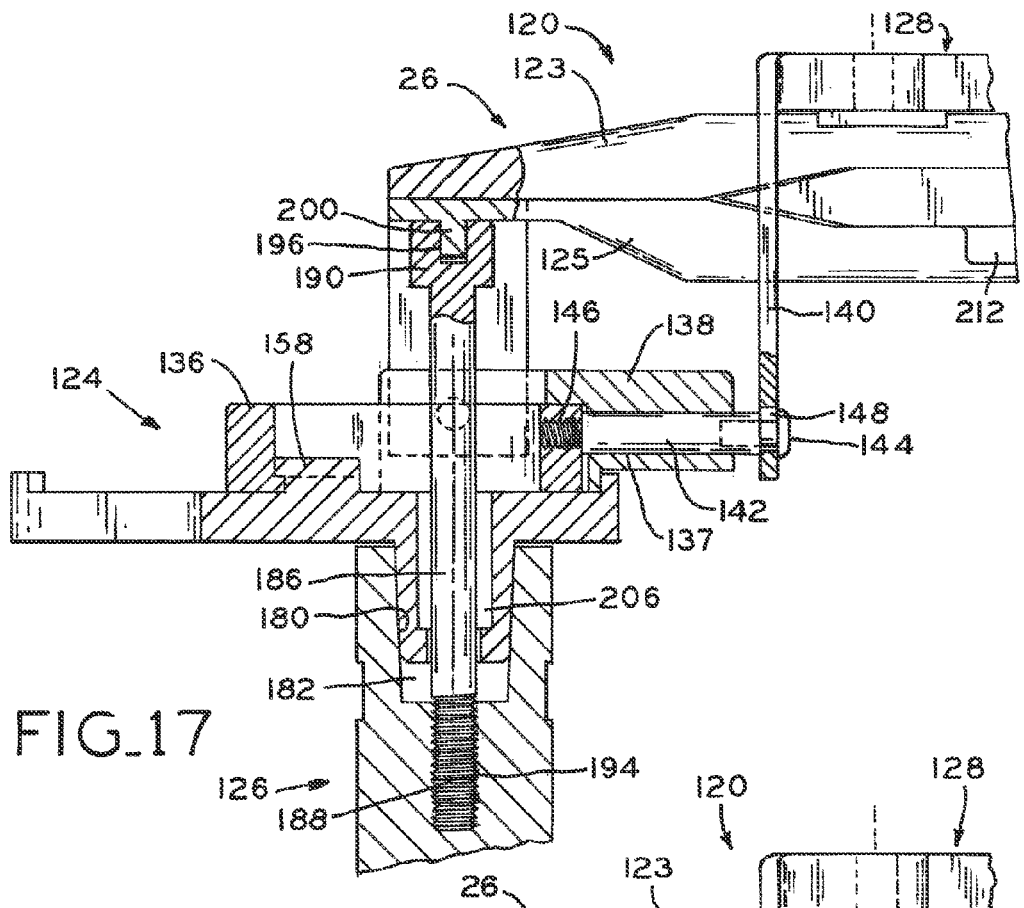
FIG_17
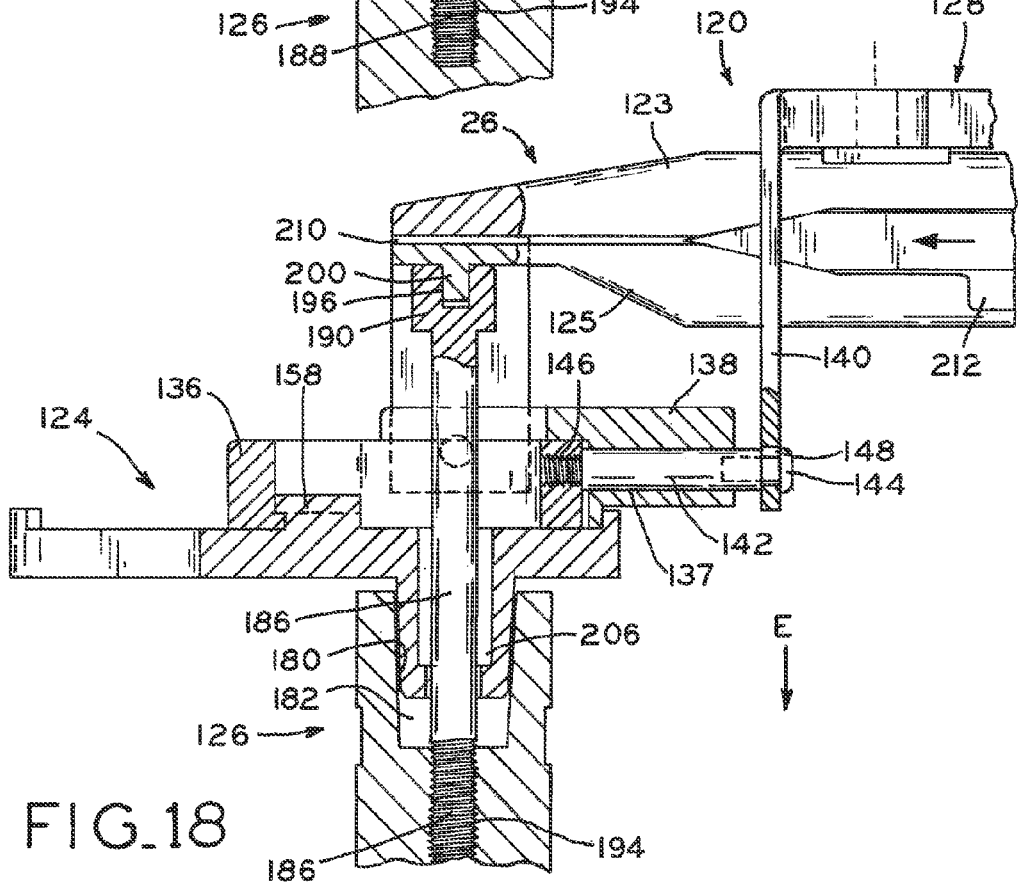
FIG_18

ORTHOPEDIC TOOL FOR ALTERING THE CONNECTION BETWEEN ORTHOPEDIC COMPONENTS

This application is a continuation of and claims the benefit of priority of U.S. patent application Ser. No. 13/875,467, filed on May 2, 2013 which applications is a continuation of and claims the benefit of priority of U.S. patent application Ser. No. 11/743,485, filed on May 2, 2007, which applications are incorporated by reference herein in their entirety.

BACKGROUND

1. Field of the Invention

The present invention relates to orthopedic tools, and, more particularly, to orthopedic tools for altering the connection between orthopedic components.

2. Description of the Related Art

Modular prostheses are commonly utilized to repair and replace damaged bone and tissue in the human body. For example, a knee prosthesis may be implanted to replace damaged or destroyed bone in the femur and/or tibia and recreate the natural, anatomical articulation of the knee joint. In modular prostheses, several individual, distinct components are connected together to form the final, implanted prosthesis. The connection between the individual, distinct components may be formed in any number of ways. For example, a first orthopedic component may include a counter bore configured to receive the head of a bolt and a second orthopedic component may include a threaded bore configured to receive the threaded shaft of the bolt. Alternatively, the first orthopedic component may have a female tapered cavity formed therein and the second orthopedic component may have a male tapered projection extending therefrom, which is configured to lockingly mate with the female tapered cavity of the first orthopedic component.

In addition to assembling individual, distinct components together to form a final, implanted prosthesis, modular systems often include different interchangeable components, e.g., several tibia plates having different characteristics, one of which is selected to be used in the final, implanted prosthesis. For example, the different tibia plates may have different thicknesses and/or orientations. This provides the surgeon greater flexible to assemble a prosthesis that more closely approximates the patient's anatomy. After the final prosthesis is assembled, and either before or after implantation, it may be necessary to replace one or more of the components to change the characteristics of the final prosthesis. Thus, it becomes necessary to separate the connection between the various orthopedic components of the modular prosthesis. If the prosthesis has been implanted, it may be advantageous to leave the orthopedic components that are not being replaced in their implanted positions. For example, during a revision surgery to replace the head of a proximal femoral prosthesis, the surgeon may leave the femoral stem implanted within the intramedullary canal of the femur, while removing and replacing the femoral head. If the components are connected via a bolt, for example, unthreading and removing the bolt may be relatively simple. However, when the components are connected via a male/female taper arrangement, it is necessary to impart a significant force to the junction between the orthopedic components to unseat the taper. Similarly, a significant force may also be required to seat the orthopedic components together.

SUMMARY

The present invention relates to orthopedic tools, and, more particularly, to orthopedic tools for altering the connection between orthopedic components. In one embodiment, the orthopedic tool of the present invention includes a housing and a wedge. The housing has a head, an upper portion, a lower portion, and openings between the upper and lower portions. The wedge is positioned at least partially between the upper portion and the lower portion of the housing and is actuatable to move toward the head of the housing. When at least a portion of the head of the housing is placed in mating engagement with the junction defined between two assembled orthopedic components, advancement of the wedge towards the head results in separation of the upper portion and lower portion of the housing. Thus, as the wedge is advanced toward the head, the upper and lower portions of the housing are separated to cause separation of the assembled orthopedic components.

In another exemplary embodiment, the orthopedic tool further includes a handle connected to the wedge. In this embodiment, movement of the handle results in corresponding movement of the wedge. In another exemplary embodiment, the head of the housing of the orthopedic tool includes teeth formed thereon. The teeth are configured for mating engagement with a corresponding indentation at or near the junction of the assembled orthopedic components. As the wedge is moved toward the head of the housing, the interaction of the teeth with the indentation at or near the junction of the assembled orthopedic components may result in the loosening of the connection therebetween.

In another exemplary embodiment, an impaction cap may be utilized. The impaction cap is configured to attach to the exterior of the housing to allow a surgeon to impact the head of the housing against the junction between the assembled orthopedic components. By utilizing an impaction cap, the connections between the housing wedge and handle are substantially shielded from the impaction force. Advantageously, this shielding increases the longevity and useful life of the orthopedic tool. Moreover, impacting the impaction cap generates and transfers vibrations directly to the junction between the orthopedic components. These vibrations facilitate the loosening of the junction between the orthopedic components.

In another exemplary embodiment, the housing of the orthopedic tool may be interchangeable with other housings. In this embodiment, a first housing may be configured to separate a first pair of orthopedic components and a second housing may be configured to separate a second pair of orthopedic component. In another exemplary embodiment, a first housing may be configured to separate the orthopedic components, while a second housing may be configured to seat the orthopedic components. For example, one housing may include a mechanism to attach to a tibial plate and separate the tibial plate from a tibial keel. Alternatively, another housing may be provided that also includes a mechanism to attach to a tibial plate, but acts to seat the tibial plate to the tibial keel.

Advantageously, the design of the present orthopedic tool provides for the altering of the connection between orthopedic components without the need for a surgeon to impart a significant force thereto. Further, this design eliminates the need for an exposed wedge or other device. Thus, the orthopedic components which remain implanted in a revision surgery, for example, are less likely to be damaged during removal of the orthopedic component being replaced and/or the subsequent seating of the new orthopedic component. Preventing damage to the remaining orthopedic components during removal helps to ensure that they will properly mate with the new orthopedic component intended to be seated thereto. Additionally, the design of the present orthopedic tool allows the surgeon to impart a separation force directly, and accurately, to the junction of the assembled orthopedic component via the head of the housing.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is an exploded perspective view of the orthopedic tool of the present invention;

FIG. 2 is a plan view of the assembled orthopedic tool of FIG. 1;

FIG. 3 is a cross sectional view of the orthopedic tool of FIG. 1 taken along line 3-3 of FIG. 2;

FIG. 4 is a cross sectional view similar to the view of FIG. 3 depicting the orthopedic tool in an actuated position;

FIG. 5 is a side view of the orthopedic tool of FIG. 2, viewed in the direction of line 5-5 in FIG. 2;

FIG. 9 is an exploded frontal view of a modular proximal femoral prosthesis;

FIG. 10 is a frontal view of the femoral prosthesis of FIG. 9 also depicting a fragmentary cross sectional view of the orthopedic tool of FIG. 1;

FIG. 11 is a frontal view of the of the prosthesis shown in FIG. 10, wherein the orthopedic tool is depicted in a fragmentary cross sectional view engaging the junction of the assembled femoral prosthesis and loosen the same;

FIG. 12 is a perspective view of an orthopedic tool according to another embodiment of the present invention, wherein the orthopedic tool is depicted engaging a modular tibial plate and keel;

FIG. 13 is an exploded view of the modular tibial plate and keel and a seating/extraction pin;

FIG. 14 is a fragmentary plan view of the orthopedic tool and modular tibial plate and keel of FIG. 12, wherein the orthopedic tool is out of engagement with the modular tibial plate;

FIG. 17 is a fragmentary, cross-sectional view depicting the orthopedic tool and modular tibial plate and keel of FIG. 12, wherein the tibial plate and keel are secured to one another and the orthopedic tool is connected thereto;

FIG. 18 is a fragmentary, cross-sectional view depicting the orthopedic tool and modular tibial plate and keel of FIG. 12, wherein the tibial plate and keel have been separated by actuation of the orthopedic tool;

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 6:
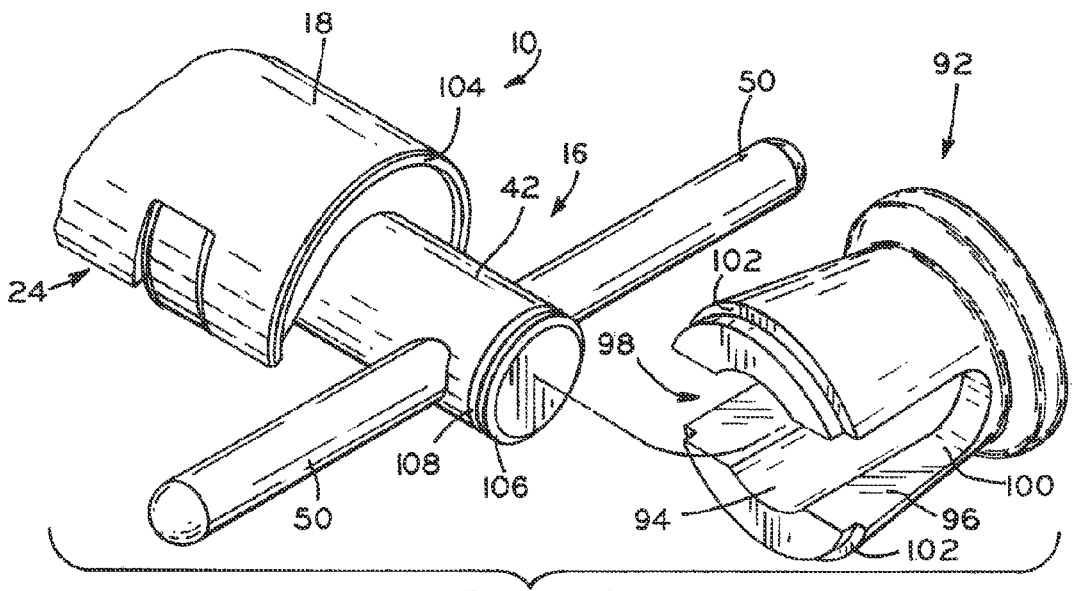
FIG. 6 is a fragmentary perspective view of the orthopedic tool of FIG. 1 further depicting an impaction cap.

FIG. 1 depicts orthopedic tool 10 according to one embodiment of the present invention. Orthopedic tool 10 includes housing 12, wedge 14, and handle 16. Additionally, orthopedic tool 10 defines longitudinal axis 17 (FIG. 3). Housing 12 further includes upper portion 18 and lower portion 20 having opening 22 extending therebetween. While the cylindrical shape of housing 12 provides an ergonomic surface for a surgeon to grip, housing 12 may be manufactured in any shape or design. Housing 12, wedge 14, and handle 16 may be formed from 17/4 (17% chromium, 4% nickel) surgical grade stainless steel. Alternatively, housing 12, wedge 14, and handle 16 may be formed from any surgical grade material capable of withstanding the forces imparted thereto during use.

Upper and lower portions 18, 20 cooperate to define body 24 and head 26 of housing 12. In one exemplary embodiment, head 26 of housing 12 further includes curved mating surface 28. In another exemplary embodiment, curved mating surface 28, configured for mating with the junction of assembled orthopedic components, includes teeth 30 formed thereon. As shown in FIG. 1, teeth 30 may be formed on both upper and lower portions 18, 20. Specifically, one of teeth 30 extends from upper portion 18 and another of teeth 30 extends from lower portion 20, directly below the one of teeth 30 extending from upper portion 18, to form a pair of teeth 30. In another exemplary embodiment, teeth 30 alternate, with one of teeth 30 extending from upper portion 18 and another of teeth 30 extending from lower portion 20 at a distanced spaced apart from the one of teeth 30 extending from upper portion 18. As described in detail below, teeth 30 are configured for mating engagement with indentations 70 (FIG. 10) formed at or near the junction of a pair of assembled orthopedic components. As shown in FIG. 5, housing 12 further includes slot 31 formed between upper and lower portions 18, 20. Slot 31 provides a separation between upper and lower portions 18, 20 at head 26. This separation, in conjunction with the separation formed by opening 22, allows for upper portion 18 and lower portion 20 to be forced apart from one another, as described in detail below.

Wedge 14 is configured for receipt within opening 22 of housing 12. Specifically, wedge 14 includes wedge head 32 and shaft 34. Wedge head 32 is configured to be advanced toward curved mating surface 28 of head 26 to separate upper and lower portions 18, 20 from one another. Specifically, when wedge 14 is advanced toward head 26, wedge head 32 forces upper portion 18 and lower portion 20 apart, causing a separation therebetween, as shown in FIG. 4. Shaft 34 of wedge 14 further includes threaded bore 36 (FIG. 4) formed therein. Additionally, slot 38 (FIG. 1) runs along at least a portion of the length of threaded bore 36 to facilitate the cleaning and sterilization of wedge 14.

Referring to FIG. 1, handle 16, designed to engage wedge 14, includes threaded shaft 40 separated from end 42 by collar 44. Threaded shaft 40 is configured to threadingly engage threaded bore 36 of wedge 14. Extending from end 42 of handle 16 are arms 50. Arms 50 form a T-shape with end 42 to facilitate the grasping and rotation of handle 16 by a surgeon. In another exemplary embodiment, an aperture (not shown) is formed in end 42 and a bar (not shown) is removeably positioned therethrough. Similar to arms 50, the bar facilitates the grasping and rotation of handle 16 by a surgeon. Handle 16 is configured for receipt within opening 22 of housing 12. Specifically, when threadingly engaged with wedge 14, handle 16 is positioned so that collar 44 is received within groove 48 of housing 12. Groove 48 allows for the rotation of handle 16 by a surgeon, while preventing translational movement of handle 16 along its longitudinal axis. In one exemplary embodiment, wedge 14 and handle 16 are formed as a single, monolithic component. In this embodiment, collar 44 is absent and handle 16 is impacted along its longitudinal axis to advance wedge 16 toward head 26 of housing 12.

As shown in FIGS. 2-3, orthopedic tool 10 is assembled with wedge 14 connected to handle 16 and positioned within opening 22 of housing 12, as described in detail above. With reference to FIG. 3, wedge head 32 is shown positioned within triangular cavity 52 extending from opening 22. As handle 16 is rotated via arms 50, the rotational movement of threaded shaft 40 will cause translational movement of wedge 14 due to the reverse threading engagement of threaded shaft 40 and threaded bore 36. Specifically, when handle 16 is rotated, wedge 14 will rotate slightly until wedge head 32 contacts at least one of walls 54, 55. Once wedge head 32 contacts at least one of walls 54, 55, rotation of wedge 14 will be prevented and handle 16 will advance wedge 14 toward curved mating surface 28 of head 26 until wedge 14 fully engages walls 54, 55 defining triangular cavity 52.

Once wedge 14 fully engages walls 54, 55, further rotation of handle 16 will continue to advance wedge 14 toward curved mating surface 28. This results in wedge 14 exerting a force on wall 54 in a first direction and exerting a force on wall 55 in a second direction, substantially opposite the first direction. As wedge 14 continues to advance, the force exerted on walls 54, 55 becomes sufficient to force upper portion 18 and lower portion 20 away from one another, as shown in FIG. 4. The separation of upper portion 18 and lower portion 20 results in the creation of gap 56 formed therebetween. When teeth 30 of curved mating surface 28 are engaged with indentations at or near the junction of assembled orthopedic components, as described in detail below, the advancement of wedge 14 and the corresponding movement of upper and lower portions 18, 20 away from one another, will result in loosening of the connection between the orthopedic components.

Figure 8:
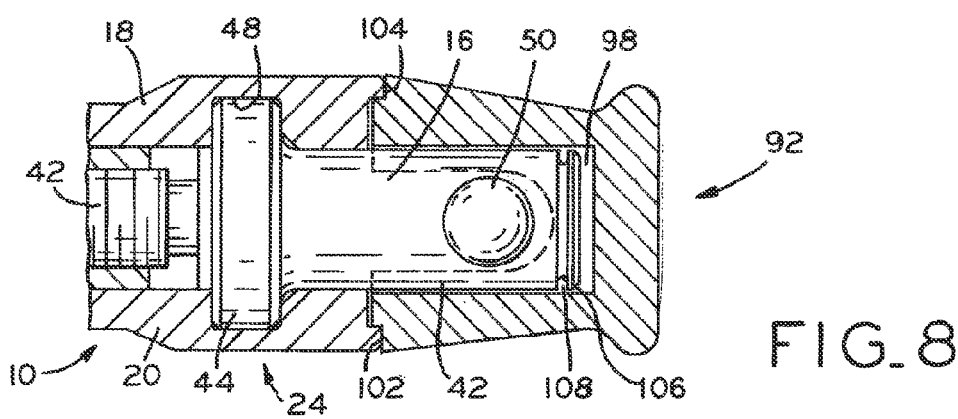
FIG. 8 is a cross sectional view of the orthopedic tool and impaction cap of FIG. 7 taken along line 8-8.

Referring to FIG. 8, orthopedic components 60 are shown as femoral head 62 and femoral stem 64. While depicted and described herein as femoral head 62 and femoral stem 64, orthopedic components 60 may be any known orthopedic components having a junction formed therebetween. Femoral head 62 is utilized in a modular femoral prosthesis to replace the natural femoral head and replicate the articulation of the same with a natural or prosthetic acetabulum. Femoral head 62 connects to femoral stem 64, which forms a part of a proximal prosthetic femur and provides an anchor for femoral head 62, to form assembled orthopedic components 60.

Femoral head 62 includes a cavity formed therein and defined by female tapered surface 66, represented by dashed lines in FIGS. 9-11. Extending downwardly from femoral head 62 are tabs 68. Tabs 68 of femoral head 62 are configured for mating engagement with indentations 70 formed in base 72 of femoral stem 64. Additionally, referring to FIG. 9, femoral stem 64 further includes male tapered surface 74 configured for mating engagement with female tapered surface 66 of femoral head 62. Female tapered surface 66 and male tapered surface 74 may be a self-locking taper, i.e., the frictional interaction between male tapered surface 74 and female tapered surface 66 will be sufficient to maintain orthopedic components 60 in its assembled condition. Once female tapered surface 66 and male tapered surface 74 of femoral head 62 and femoral stem 64, respectively, have been seated, significant force is required to loosen the connection. While described and depicted herein as a tapered connection, the connection between orthopedic components 60 may be any known connection which requires the application of a force to the junction between the orthopedic components to loosen the connection therebetween.

Once assembled, as shown in FIG. 9, bottom surface 76 of femoral head 62 forms junction 78 (FIG. 10) with shoulder 80 of femoral stem 64. Femoral head 62 has substantially fewer tabs 68 than femoral stem 64 has indentions 70. Thus, indentions 70 provide a rotational lock for femoral head 62. Specifically, with tabs 68 inserted within indentions 70, femoral head 62 is prevented from rotating relative to femoral stem 64. Moreover, if femoral head 62 had an eccentric or asymmetrical configuration, the eccentric or asymmetrical positioning of femoral head 62 may be altered by rotating femoral head 62 to align tabs 68 with various indentations 70 of femoral stem 64. In this manner, tabs 68 and indentations 70 allow for varying the rotational alignment of femoral head 62 with respect to femoral stem 64 between a plurality of predetermined positions.

In another exemplary embodiment, femoral head 62 lacks tabs 68 and can be infinitely rotated upon tapered surface 74 of femoral stem 64 prior to seating of the corresponding tapered surfaces 66, 74. In this embodiment, teeth 30 are configured to mate with indentations 70 of femoral stem 64 to loosen the connection between femoral head 62 and femoral stem 64, as described in detail below. In another exemplary embodiment, indentations 70 may extend across junction 78 and into femoral head 62. Thus, when aligned, orthopedic tool 10 may be utilized to engage indentations 70 of both femoral head 62 and femoral stem 64 to loosen the connection therebetween. In yet another exemplary embodiment, teeth 30 of head 26 of housing 12 are angled to form a wedge shape. In this embodiment, teeth 30 may be impacted into junction 78 between the assembled orthopedic components 60. This allows orthopedic tool 10 to be used to loosen the connection between orthopedic components 60 which lack indentations 70.

Referring to FIGS. 9-11, orthopedic tool 10 may be aligned such that teeth 30 of head 26 matingly engage indentations 70 of femoral stem 64. Advantageously, the use of teeth 30 and indentations 70 limit rotational and translational movement of orthopedic tool 10 during use. With orthopedic tool 10 matingly engaged with indentations 70 of femoral stem 64, as shown in FIG. 10, handle 16 (FIG. 1) may be actuated to advance wedge head 32 toward curved mating surface 28. As shown in FIG. 10, teeth 30 are received within empty indentations 70. In one exemplary embodiment, teeth 30 may be configured with space 82 (FIG. 2) formed therebetween. Space 82 will accommodate one of indentations 70 having one of tabs 68 seated therein. Thus, orthopedic tool 10 may be utilized to engage any exposed indentations 70, even if one of indentations 70 is occupied by one of tabs 68. As wedge head 32 is advanced, the force exerted on upper and lower portions 18, 20 causes separation of upper and lower portions 18, 20 and the creation of gap 56 therebetween. As gap 56 increases, upper edges 84 and lower edges 86 of teeth 30 (FIG. 10) will engage bottom surface 76 (FIG. 9) of femoral head 62 and bottom walls 88 (FIG. 10) partially defining indentations 70 in femoral stem 64. Thus, as the force exerted by teeth 30 increases, with the corresponding movement of wedge 14 toward curved mating surface 28, the connection along junction 78 of orthopedic components 60 will loosen to form gap 90 (FIG. 11). Advantageously, utilizing orthopedic tool 10 prevents significant forces being exerted on orthopedic components 60 due to impaction of a wedge directly against junction 78.

Figure 7:
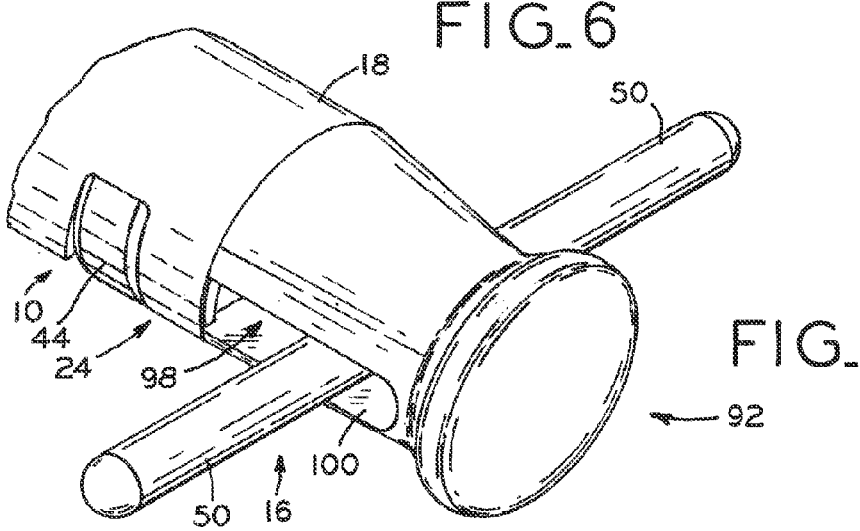
FIG. 7 is a fragmentary perspective view showing the orthopedic tool and the impaction cap connected thereto.

Referring to FIGS. 6-8, to further facilitate the loosening of the connection between femoral head 62 and femoral stem 64, impaction cap 92 may be used. Impaction cap 92 includes groove 94 and arcuate sidewalls 96 forming cavity 98, as shown in FIG. 6. Arcuate sidewalls 96 further define slots 100 configured for the receipt of arms 50. Receipt of arms 50 within slots 100 restricts rotation of handle 16 to keep handle 16 and, correspondingly, wedge 14 in a substantially fixed position. Impaction cap 92 further includes shoulder 102 configured to rest upon ledge 104 of housing 12. When impaction cap 92 is seated on housing 12, as shown in FIG. 6, wedge 104 is in contact with shoulder 102 and arms 50 are received within slot 100.

As shown in FIG. 6, end 42 of handle 16 further includes ridge 106 formed therein. Ridge 106 defines a first edge of groove 108, which may receive an O-ring (not shown) therein. The O-ring received with groove 108 of handle 16 may act as a retention mechanism, which provides a friction fit between the O-ring and arcuate sidewalls 96 of impaction cap 92. This allows a surgeon to fixedly seat impaction cap 92 upon housing 12 and provides for the retention of the same thereon. In this position, impaction cap 92 may be impacted by a surgeon, such as by striking the head of impaction cap 92 with a hammer, for example. Use of impaction cap 92 allows for the transfer the impaction force, generated when a surgeon strikes impaction cap 92, substantially entirely to housing 12 and junction 78. Thus, threaded shaft 40 of handle 16 and threaded bore 36 of wedge 14 are not subjected to any of the impaction force resulting from the surgeon striking impaction cap 92. Advantageously, preventing the impaction force from being applied to threaded shaft 40 and threaded bore 36 prevents damage thereto and increases the useful life and longevity of orthopedic tool 10. Moreover, the impaction of impaction cap 92 generations vibrations which are transferred to junction 78 via housing 12. Advantageously, these vibrations facilitate the loosening of the connection between femoral head 62 and femoral stem 64.

Another exemplary embodiment of orthopedic tool 10 is depicted in FIG. 12 as orthopedic tool 120. Orthopedic tool 120 is also utilized to separate orthopedic components and includes housing 122 having upper portion 123 and lower portion 125. Housing 122 has several components that are identical or substantially identical to corresponding components of housing 12 of FIGS. 1-5 and corresponding reference numerals have been used to identify identical or substantially identical components therebetween. Housing 122 is configured for use with wedge 14 and handle 16 of orthopedic tool 10. Thus, by removing wedge 14 and handle 16 from housing 12 and assembling wedge 14 and handle 16 within housing 120, in the same manner as described above with respect to the assembly of orthopedic tool 10, orthopedic tool 120 is formed.

As shown in FIG. 12, orthopedic tool 120 is configured to matingly engage an orthopedic component, such as modular tibial plate and keel components 124, 126, respectively. Tibial plate and keel components 124, 126 are utilized in a modular tibial prosthesis to replace the proximal portion of the tibia and replicate the articulation of the same with a natural or prosthetic distal femur. Tibial plate 124 connects to tibial keel 126, which provides an anchor for tibial plate 124, to form a portion of a modular tibial prosthesis. Referring to FIG. 17, modular tibial plate 124 includes male tapered portion 180 configured for receipt within female tapered bore 182 of modular tibial keel 126. Male tapered portion 180 and female tapered bore 182 may form a self-locking taper connection, i.e., the frictional interaction between male tapered portion 180 and female tapered bore 182 will be sufficient to maintain the orthopedic components in an assembled condition. While described and depicted herein as a tapered connection, the connection between modular tibial plate and keel 124, 126 may be any known connection which requires the application of a force to the junction between the orthopedic components to loosen the connection therebetween.

Referring to FIG. 13, to facilitate the separation and/or seating of modular tibial plate and keel components 124, 126, pin 184 is utilized. Pin 184 includes shaft 186 having threaded portion 188 and head 190. Exterior 192 of head 190 may be knurled to facilitate the grasping and manipulation of pin 184 by a surgeon. Referring to FIG. 17, threaded portion 188 of pin 184 is configured to threadingly engage threaded bore 194 of tibial keel 126. Additionally, head 190 includes bore 196 formed therein. Bore 196 of head 190 may be configured as a hexagonal bore to matingly engage a corresponding drive tool (not shown), for example. Bore 196 of head 190 may also be configured to receive projection 200 (FIG. 17) of lower portion 125 of housing 120 therein. Extending from modular tibial plate 124 is bracket 158, which is configured to facilitate securement of orthopedic tool 120 to tibial plate 124, as described in detail below.

As shown in FIG. 12, housing 122 of orthopedic tool 120 includes handle 128 having aperture 130 formed therein. Received within aperture 130 is pivot pin 132 extending from upper portion 123 of housing 122. By actuating handle 128 against the biasing force of spring fingers 160, 162, slider 136, formed within base 138 of housing 122, is moved from an open, non-engagement position to a closed, engagement position relative to bracket 158 of tibial plate 124. Slider 136 is connected to arm 140 of handle 128 via threaded pin 142 and screw 144. As shown in FIG. 17, threaded pin 142 extends through aperture 137 in base 138 to threadingly engage aperture 146 formed in slider 136. Screw 144 extends through slot 148 in arm 140 and threadingly engages bore 150 of threaded pin 142 to secure threaded pin 142 and, correspondingly, slider 136 to arm 140 of handle 128.

Figure 15:
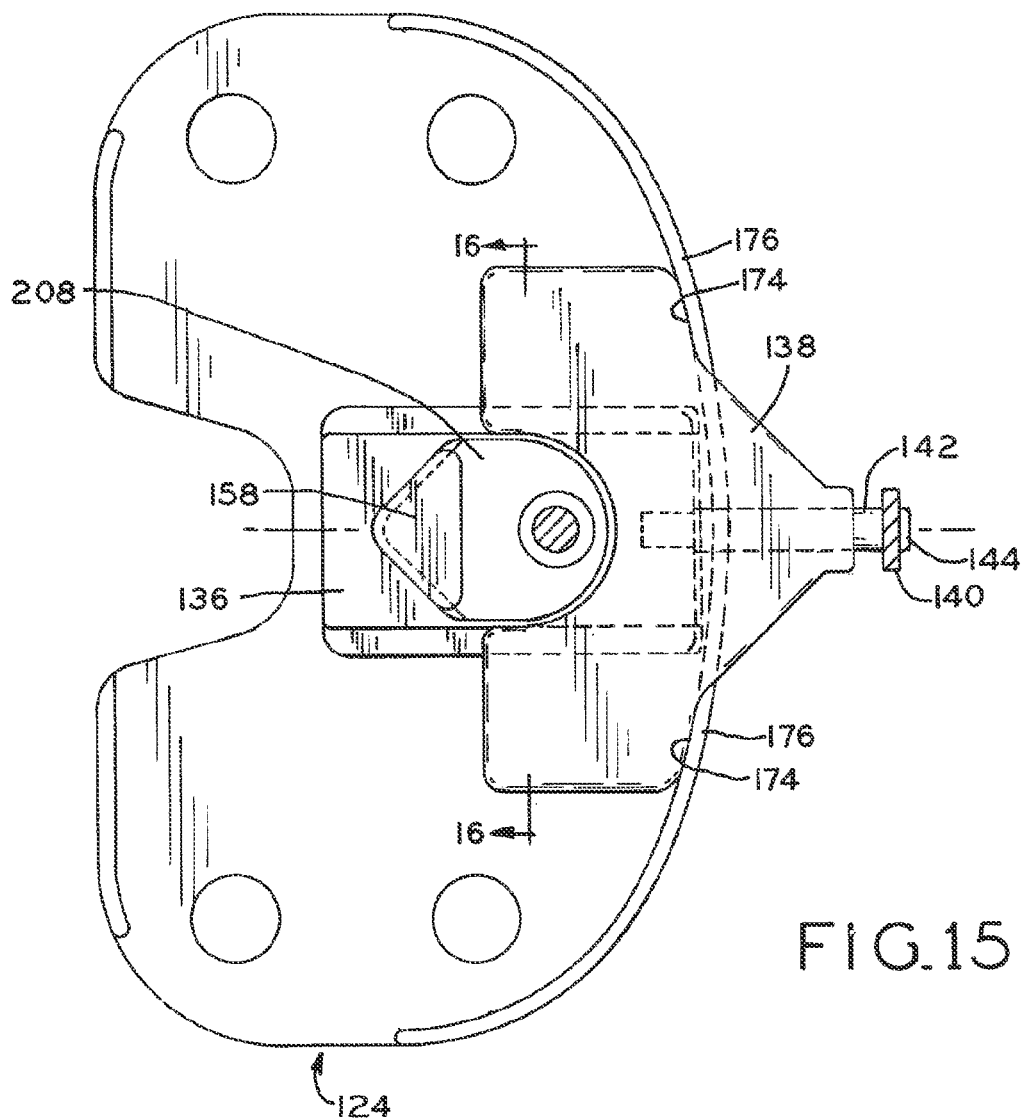
FIG. 15 is a fragmentary plan view of the orthopedic tool and modular tibial plate and keel of FIG. 12, wherein the orthopedic tool is engaged with the modular tibial plate.
Figure 16:
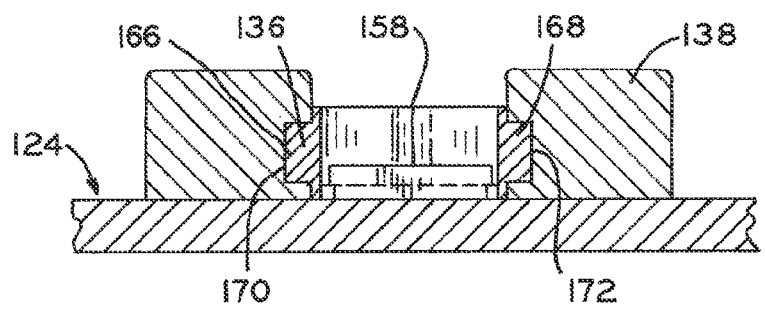
FIG. 16 is a fragmentary, cross-sectional view taken along line 16-16 of FIG. 15.

Referring to FIG. 14, slider 136 is shown in the open, non-engagement position. Specifically, gap 152 is formed between projection 154 of slider 136 and cutout 156 (shown in dashed lines in FIG. 14) of bracket 158 of tibial plate 124. To position slider 136 in the open, non-engagement position, handle 128 is actuated to move handle 128 in the direction of arrow A (FIG. 12) and toward housing 122. For example, handle 128 may be actuated by the gripping of handle 128 by a surgeon. In this manner, slider 136 is advanced in the direction of arrow B (FIG. 14) until gap 152 is created and projection 154 of slider 136 is removed from cutout 156 of bracket 158. By releasing handle 128, spring fingers 160, 162 of handle 128 and block 164, respectively, act to bias handle 128 outward in the direction of arrow C (FIG. 12) and away from housing 122. Specifically, ends 161, 163 of spring fingers 160, 162, respectively, act against block 165 and inner surface 167 of handle 128, respectively. This results in corresponding movement of slider 136 in the direction of arrow D (FIG. 14), moving slider 136 into the closed, engagement position and moving projection 154 of slider 126 into cutout 156 of bracket 158, as shown in FIG. 15. To facilitate linear movement of slider 136, slider 136 includes projections 166, 168 configured for receipt within grooves 170, 172 (FIG. 16) formed in base 138. Thus, as slider 126 is moved from the closed, non-engagement position to the open, engagement position and vice versa, projections 166, 168 move within grooves 170, 172 of base 138 and direct slider 136 on a linear path defined by base 138.

Referring to FIG. 12, base 138 of orthopedic tool 120 is rigidly connected to arms 202 of upper portion 123 of housing 122 via pins 204. Pins 204 extend through apertures (not shown) in arms 202 and base 138. In one exemplary embodiment, pins 204 are threaded to threadingly engage an aperture (not shown) in base 138. While described and depicted herein as connected by pins 204, arms 202 and base 138 may be formed as an integral, monolithic structure. Referring to FIGS. 14 and 15, base 138 further includes end wall 174 having a curvature substantially similar to the curvature of ledge 176 of tibial plate 124. Thus, end wall 174 of base 138 may be placed in mating engagement with ledge 176 of tibial plate 124 to further indicate that orthopedic tool 120 is properly aligned relative to tibial plate 124.

To separate modular tibial plate and keel 124, 126 from one another, threaded portion 188 of pin 184, shown in FIGS. 13 and 17, is inserted through aperture 206 in tibial plate 124 and female tapered bore 182 of tibial keel 126. Threaded portion 188 is advanced to threadingly engage threaded bore 194 of tibial keel 126. To advance pin 184 into threaded bore 194, a surgeon may grasp knurled exterior 192 of pin 184. Alternatively, a drive tool (not shown) may be engaged with bore 196 of pin 184. Once pin 184 is threadingly engaged with tibial keel 126, orthopedic tool 120 may be connected to tibial plate and keel 124, 126. Specifically, handle 128 is actuated to place slider 136 in the open, non-engagement position. Orthopedic tool 120 may then be positioned over tibial plate and keel 124, 126 with pin 184 and bracket 158 aligned within cutout 208 (FIGS. 14 and 15) formed by slider 136 and base 138. As orthopedic tool 120 is advanced toward tibial plate 124, projection 200 of lower housing 125 is seated within bore 196 of pin 184 and end wall 174 of base 138 is placed in mating contact with ledge 178 of tibial plate 124. Once positioned as described above, the surgeon may release handle 128, causing handle 128 to be biased in the direction of arrow C of FIG. 12. As a result of the biasing of handle 128, slider 136 is advanced into engagement with bracket 158, allowing projection 154 of slider 136 to be received within cutout 156 of bracket 158.

Once properly positioned relative to the orthopedic components, such as tibial plate and keel 124, 126, orthopedic tool 120 is utilized in a substantially similar manner as orthopedic tool 10 to separate the orthopedic components. As shown in FIG. 17, tibial plate and keel 124, 126 are shown in a seated position. To separate tibial plate and keel 124, 126, wedge 14 is advanced as described in detail above with respect to orthopedic tool 10. However, unlike housing 12 of orthopedic tool 10, in which upper portion 18 and lower portion 20 separated from one another at the same rate, lower portion 125 of housing 122 is more likely to separate from upper portion 123 to create gap 210.

As shown in FIGS. 17 and 18, lower portion 125 includes cutout 212. Cutout 212 changes the properties of lower portion 125 by decreasing the thickness of lower portion 125 and making it more flexible than upper portion 123. In another exemplary embodiment, lower portion 125 lacks cutout 212 and upper and lower portions 123, 125 are formed from different materials having different material properties, resulting in lower portion 125 being more flexible than upper portion 123. As a result of the greater flexibility of lower portion 125, when wedge 14 is advanced, upper portion 123 and, correspondingly base 138 and tibial plate 124, remain substantially stationary, while lower portion 125 and, correspondingly, tibial pin 184 and tibial keel 126 are advanced in the direction of arrow E (FIG. 18). Specifically, movement of lower portion 125 exerts a force on head 190 of pin 184. Pin 184, in turn, transfers the same force to threaded bore 194 and tibial keel 126, causing tibial keel 126 to be forced away from tibial plate 124. As a result of the advancement of tibial keel 126, tibial plate 124 and tibial keel 126 are separated from one another.

Figure 19:
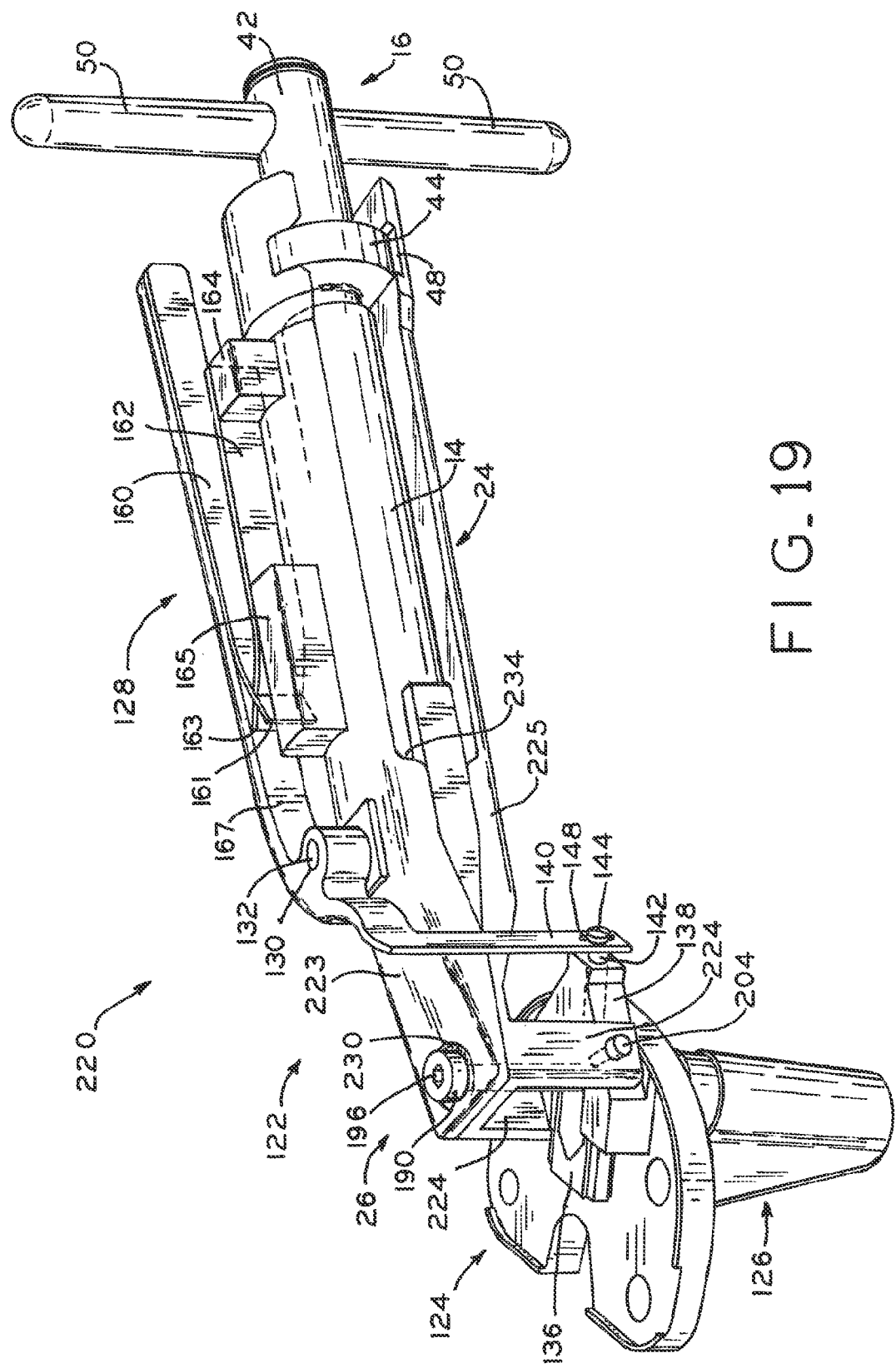
FIG. 19 is a perspective view of a orthopedic tool according to another embodiment of the present invention, wherein the orthopedic tool is depicted engaging a modular tibial plate and keel.
Figure 20:
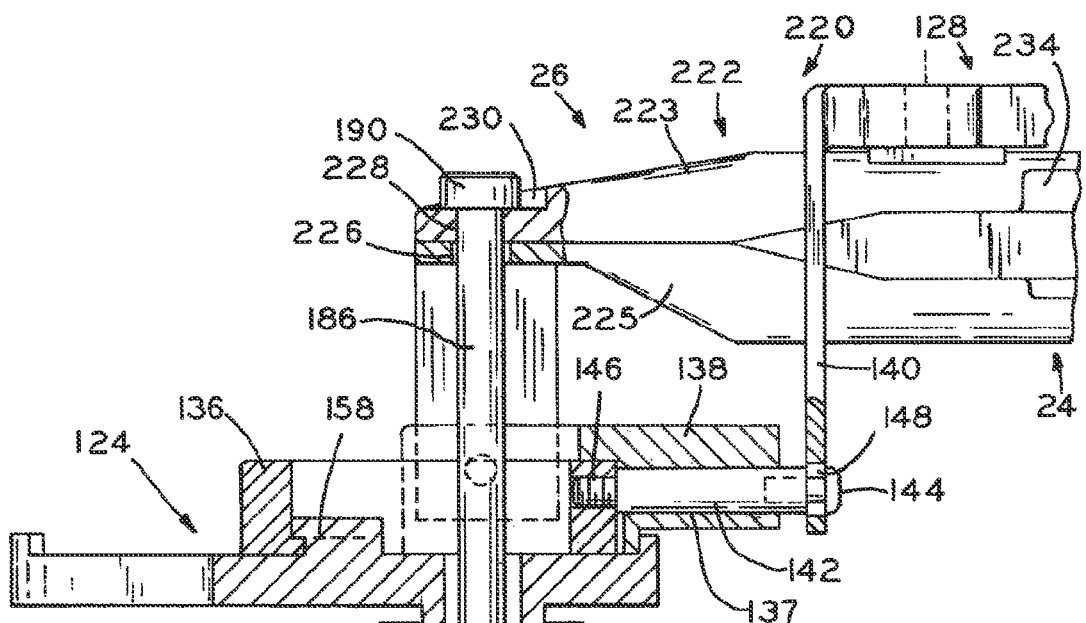
FIG. 20 is a fragmentary, cross-sectional view depicting the orthopedic tool and modular tibial plate and keel of FIG. 19, wherein the tibial plate and keel are separated.

Another exemplary embodiment of orthopedic tool 120 is depicted in FIG. 19 as orthopedic tool 220. Orthopedic tool 220 is utilized to seat orthopedic components and includes housing 222 having upper portion 223 and lower portion 225. Similar to housing 120, housing 220 is configured for use with wedge 14 and handle 16 of orthopedic tool 10. Thus, be removing wedge 14 and handle 16 from housing 12 and assembling wedge 14 and handle 16 within housing 222, in the same manner as described above with respect to orthopedic tool 10, orthopedic tool 220 is formed.

Figure 21:
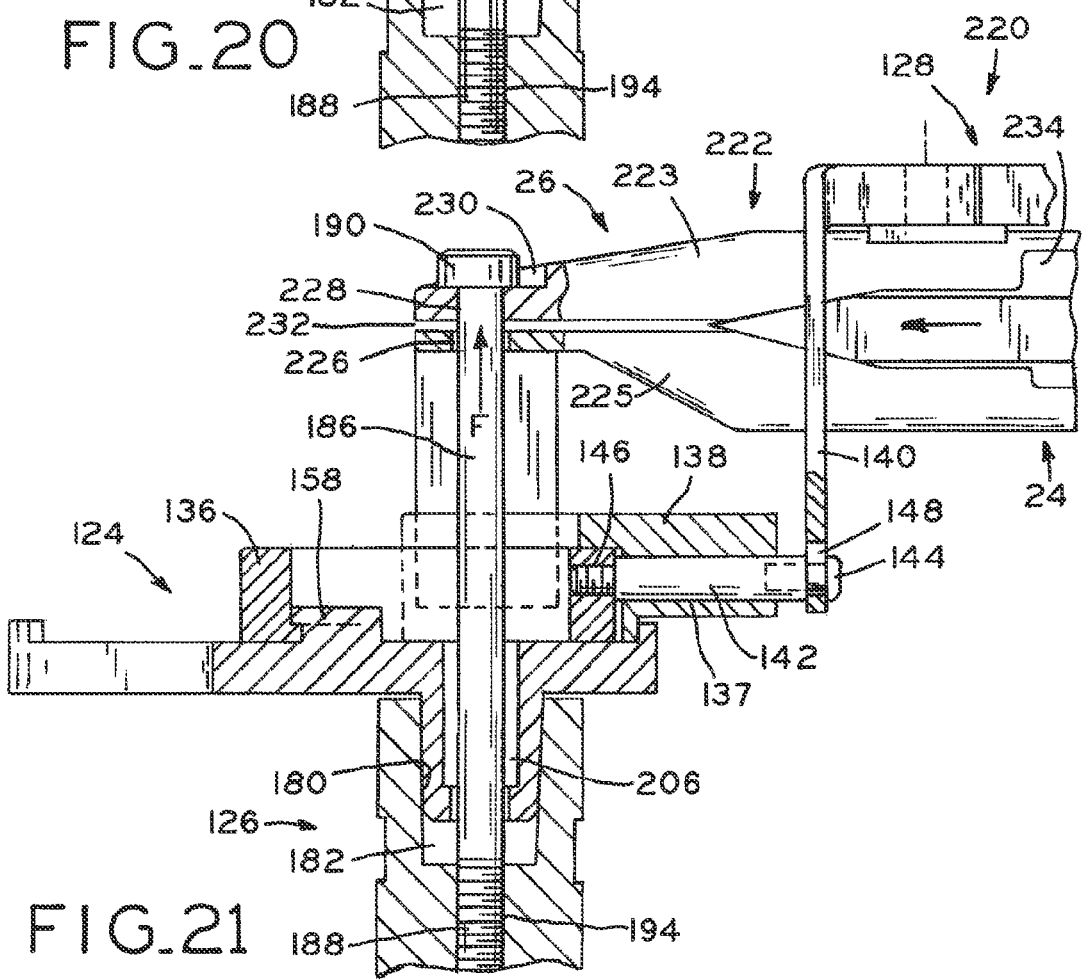
FIG. 21 is a fragmentary, cross-sectional view depicting the orthopedic tool and modular tibial plate and keel of FIG. 19, wherein the tibial plate and keel have been seated by actuation of the orthopedic tool.

Housing 222 has several components that are identical or substantially identical to corresponding components of housing 122 of FIG. 12 and corresponding reference numerals have been used to identify identical or substantially identical components therebetween. For example, housing 222 includes slider 136 and base 138 that facilitate the attachment of orthopedic tool 220 to orthopedic components, such as tibial plate and keel 124, 126, in the same manner as described in detail above with respect to orthopedic tool 120. However, in contrast to arms 202 of housing 122 of orthopedic tool 120, housing 222 of orthopedic tool 220 includes arms 224 extending from lower portion 225. Arms 224 are connected to base 138 via pins 204 as described in detail above with respect to housing 120. Additionally, as shown in FIG. 21, lower portion 225 of housing 222 includes aperture 226 extending therethrough. Collinear with aperture 226 is aperture 228, which extends through upper portion 223 of housing 222 and includes counter bore 230. Apertures 226, 228 are sized to receive shaft 186 of pin 184 therethrough and counter bore 230 is sized to receive head 190 of pin 184 therein.

Referring to FIGS. 21 and 22, to seat orthopedic components, such as tibial plate 124 and tibial keel 126, orthopedic tool 220 is secured to bracket 158 of tibial plate 124 in the same manner as described in detail above with respect to orthopedic tool 120. Once secured to bracket 158 of tibial plate 124, pin 186 is advanced through apertures 226, 228 in upper and lower portions 223, 225 of housing 222 and threaded portion 188 of pin 186 is threadingly engaged with threaded bore 194 in tibial keel 126 as described in detail above. With pin 186 threadingly engaged with threaded bore 194, pin 184 is threadingly advanced until head 190 of pin 184 is seated within counter bore 230 of upper portion 223 of housing 222.

Once properly connected to an orthopedic component, such as tibial plate and keel 124, 126, orthopedic tool 220 is utilized in a substantially similar manner as orthopedic tool 120. However, in contrast to orthopedic tools 10 and 120, which separate the orthopedic components, orthopedic tool 220 seats the orthopedic components. As shown in FIG. 17, tibial plate and keel 124, 126 are shown in a separated position. To seat tibial plate and keel 124, 126, wedge 14 is advanced as described in detail above with respect to orthopedic tool 10. However, unlike housing 12 of orthopedic tool 10, in which upper portion 18 and lowr portion 20 separated from one another at the same rate, upper portion 223 of housing 222 will separate from lower portion 225 to create gap 232.

Specifically, as shown in FIGS. 17 and 18, upper portion 223 includes cutout 234. Similar to cutout 212 of lower portion 125 of housing 122, cutout 234 changes the properties of upper portion 223 of housing 222 by decreasing the thickness of upper portion 223 and making upper portion 223 more flexible than lower portion 225. In another exemplary embodiment, upper portion 223 lacks cutout 234 and upper and lower portions 223, 225 are formed from different materials having different material properties, resulting in upper portion 223 being more flexible than lower portion 225. As a result of the greater flexibility of upper portion 223, when wedge 14 is advanced, lower portion 225 and, correspondingly base 138 and tibial plate 124, remain substantially stationary, while upper portion 223 and, correspondingly, pin 184 and tibial keel 126 are advanced in the direction of arrow F (FIG. 21). Specifically, movement of upper portion 223 exerts a force on head 190 of pin 184. Pin 184, in turn, transfers the same force to threaded bore 194 and tibial keel 126, causing tibial keel 126 to be forced toward tibial plate 124. As a result of the advancement of tibial keel 126, tibial plate 124 and tibial keel 126 are seated together.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of altering a connection between components of an orthopedic implant comprising:
   providing or obtaining an orthopedic tool that includes an elongate housing that defines a longitudinal axis and includes an upper portion, a lower portion at least partially separable from the upper portion, a head, a wedge positioned between the upper portion and the lower portion of the elongate housing, and a handle extending from the wedege to beyond a proximal end of the elongate housing;
   engaging the upper portion of the elongate housing to a first component of the orthopedic implant and the lower portion of the elongate housing to a second component of the orthopedic implant, wherein the first component and the second component are in a connected relationship with one another;
   advancing the wedge distally along the longitudinal axis of the elongate housing toward the head in order to separate the upper portion from the lower portion thereby altering the connected relationship between the first component and the second component;
   attaching an impaction cap to the elongate housing by directly contacting an impact transfer surface of the impaction cap to the proximal end of the elongate housing, wherein a cavity is defined between the impaction cap and the handle; and
   applying an impaction force to an outer cap impaction surface of the impaction cap that is disposed generally opposite the impact transfer surface, wherein the impaction force is transferred substatially entirely through the elongate housing to the first and second components.

2. The method of claim 1, wherein advancing the wedge distally along the longitudinal axis includes rotating the handle relative to the housing about the longitudinal axis.

3. The method of claim 2, wherein the handle is restricted from translating along the longitudinal axis of the housing when the handle is rotated relative to the housing.

4. The method of claim 2, wherein the handle is secured within the housing with a collar and a groove.

5. The method of claim 4, wherein the handle defines the collar and the housing defines the groove.

6. The method of claim 2, wherein the handle includes an externally threaded shaft portion and the wedge includes a threaded bore and wherein the externally threaded shaft portion is engaged with the threaded bore.

7. The method of claim 6, wherein the shaft portion and the bore are in a reverse threading engagement.

8. The method of claim 2, wherein advancing the wedge distally along the longitudinal axis includes driving the wedge into the head to at least partially separate the lower portion from the upper portion.

9. The method of claim 1, wherein altering the connected relationship includes loosening the first component from the second component.

10. The method of claim 1, wherein the orthopedic tool further includes an opening defined by an outer surface of a sidewall of the housing and the opening is configured to receive the wedge.

11. The method of claim 10, wherein the opening extends from the proximal end of the housing to a point in the outer surface of the sidewall that is distal to the proximal end.

12. The method of claim 1, wherein engaging the upper portion to the first component of the orthopedic implant and the lower portion to the second component of the orthopedic implant includes engaging a pair of teeth extending from the housing with complementary indentations in the first and second components.

13. The method of claim 1, wherein the head further includes a curved surface configured to engage the components of the orthopedic implant adjacent to a junction surface.

14. The method of claim 1, the impaction cap further comprising at least one slot sized to receive the handle, the slot resisting the movement of the handle when the impaction cap is removably attached to the proximal end of the elongate housing.

15. A method of altering a connection between components of an orthopedic implant comprising:
   providing or obtaining an orthopedic tool that includes an elongate housing that defines a longitudinal axis and includes an upper portion, a lower portion at least partially separable from the upper portion, a head, an opening defined in an outer surface of a sidewall of the housing, a wedge sized to pass through the opening and positioned between the upper poriton and the lower portion of the elongate housing, a handle secured within the housing with a collar and groove and extending from the wedge to beyond a proximal end of the elongate housing, and an impaction cap that is configured to be removably attached to the elongate housing, wherein the impaction cap includes an outer cap impaction surface and an impact transfer surface disposed generally opposite the outer cap impaction surface;

engaging the upper portion to a first component of the orthopedic implant and the lower portion to a second component of the orthopedic implant, wherein the first component and the second component are in a connected relationship with one another;

rotating the handle relative to the housing about the longitudinal axis to advance the wedge distally along the longitudinal axis of the elongate housing and separate the upper portion from the lower portion, thereby altering the connected relationship between the first component and the second component, wherein the handle is restricted from translating along the longitudinal axis of the housing when the handle is rotated relative to the housing;

attaching the impaction cap to the proximal end of the elongate housing, wherein a cavity is defined between the impaction cap and the handle; and applying an impaction force to the outer cap impaction surface of the impaction cap, wherein the impaction force is transferred substantially entirely through the elongate housing to the first and second components.

16. The method of claim 15, wherein the opening extends from the proximal end of the housing to a point in the outer surface of the sidewall that is distal to the proximal end.

17. The method of claim 15, the impaction cap further comprsing at least one slot sized to receive the handle, the slot resisting the movement of the handle when the impaction cap is removably attached to the proximal end of the elongate housing.

* * * * *

UNITED STATES PATENT AND TRADEMARK OFFICE
CERTIFICATE OF CORRECTION

PATENT NO.         : 9,615,941 B2                                                Page 1 of 1
APPLICATION NO.    : 14/704358
DATED              : April 11, 2017
INVENTOR(S)        : Meek et al.

It is certified that error appears in the above-identified patent and that said Letters Patent is hereby corrected as shown below:

In Column 11, Line 60, in Claim 1, delete "wedege" and insert --wedge-- therefor In Column 12, Line 14, in Claim 1, delete "substatially" and insert --substantially-- therefor In Column 13, Line 3, in Claim 15, delete "poriton" and insert --portion-- therefor In Column 14, Line 16, in Claim 17, delete "comprsing" and insert --comprising-- therefor Signed and Sealed this
Seventeenth Day of April, 2018

Andrei Iancu
*Director of the United States Patent and Trademark Office*